United States Patent [19]

Baker

[11] Patent Number: 5,405,825
[45] Date of Patent: Apr. 11, 1995

[54] EMULSIFIABLE SUSPENSION CONCENTRATE COMPOSITIONS OF IMIDAZOLINYL BENZOIC ACIDS, ESTERS AND SALTS THEREOF, AND DINITROANILINE HERBICIDES

[75] Inventor: Ivor P. Baker, Chandlers Ford, England

[73] Assignee: American Cyanamid Co., Wayne, N.J.

[21] Appl. No.: 128,443

[22] Filed: Sep. 28, 1993

[51] Int. Cl.$^6$ .................. A01N 43/50; A01N 33/08
[52] U.S. Cl. .................. 504/139; 504/116; 504/130; 504/148
[58] Field of Search .................. 504/116, 130, 148, 139

[56] References Cited

U.S. PATENT DOCUMENTS

| | | | |
|---|---|---|---|
| 4,871,388 | 10/1989 | Pasarela et al. | 504/130 |
| 5,073,189 | 12/1991 | Bell | 71/DIG. 1 |
| 5,270,286 | 12/1993 | Ong | 504/130 |

FOREIGN PATENT DOCUMENTS

420497-A1  9/1990  United Kingdom.

*Primary Examiner*—Allen J. Robinson
*Assistant Examiner*—Brian G. Bembenick

[57] ABSTRACT

The present invention provides herbicidal emulsifiable suspension concentrate compositions of imidazolinyl benzoic acids, or esters or salts thereof, and dinitroaniline herbicides which have improved low temperature stability.

13 Claims, No Drawings

EMULSIFIABLE SUSPENSION CONCENTRATE COMPOSITIONS OF IMIDAZOLINYL BENZOIC ACIDS, ESTERS AND SALTS THEREOF, AND DINITROANILINE HERBICIDES

BACKGROUND OF THE INVENTION

Combination products containing imidazolinyl benzoic acids, or esters or salts thereof, such as imazamethabenz-methyl (an isomeric mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate), and dinitroaniline herbicides, such as pendimethalin (N-(1-ethylpropyl)-2,6-dinitro-3,4-xylidine), trifluralin (N,N-dipropyl-2,6-dinitro-4-trifluoromethylaniline) and the like, are effective herbicidal agents. However, it has been found that those combination products exhibit poor low temperature stability. Those products tend to thicken on storage at low temperatures and solid product remains in the container after use. The agriculturalist may experience difficulty, therefore, when using those products (e.g., during application of the herbicide, or with special storage requirements and limited application times).

Efforts to overcome the problems of the prior art are described in commonly assigned, copending U.S. patent application Ser. No. 648,083, filed on Jan. 31, 1991 (now U.S. Pat. No. 5,270,286).

The present invention overcomes the drawbacks of the prior art by providing a herbicidal emulsifiable suspension concentrate composition which exhibits low temperature stability. Such stable compositions also have desirable flow characteristics.

It is an object of the present invention, therefore, to provide an emulsifiable suspension concentrate composition of imidazolinyl benzoic acids, or esters or salts thereof, and dinitroaniline herbicides, which is stable at low temperatures.

SUMMARY OF THE INVENTION

The present invention relates to a herbicidal emulsifiable suspension concentrate composition comprising about 5% to 20% by weight of a imdazolinyl benzoic acid, or ester or salt thereof, about 10% to 30% by weight of a dinitroaniline herbicide, about 2% to 10% by weight of an alkylarylsulfonate, about 0.5% to 10% by weight of an antigelation agent, about 5% to 15% by weight of a nonionic surfactant or mixture of nonionic surfactants, about 1% to 10% by weight of a suspending agent, up to about 1% by weight of an antifoaming agent, and an organic solvent or mixture of organic solvents.

DETAILED DESCRIPTION OF THE INVENTION

It has been found that combinations of herbicidal imidazolinyl benzoic acids, or esters or salts thereof, and dinitroaniline emulsifiable suspension concentrate compositions thicken on storage at low temperatures and that large amounts of product are left in the container after the contents are poured out. Since those compositions may be used in areas where low temperature prevails, emulsifiable suspension concentrate compositions with low temperature stability are required. Surprisingly, it has now been discovered that the herbicidal emulsifiable suspension concentrate compositions of the present invention remain free-flowing at low temperatures and do not leave any significant amounts of product in the container after pouring.

The herbicidal emulsifiable suspension concentrate compositions of the present invention comprise about 5% to 20% by weight imidazolinyl benzoic acids, or esters or salts thereof, such as imazamethabenz-methyl, about 10% to 30% by weight of a dinitroaniline herbicide, such as pendimethalin or trifluralin, about 2% to 10% by weight of an alkylarylsulfonate, about 0.5% to 10% by weight of an antigelation agent, about 5% to 15% by weight of a nonionic surfactant or mixture of nonionic surfactants, about 1% to 10% by weight of a suspending agent, up to about 1% by weight of an antifoaming agent, and an aromatic solvent or mixture of aromatic solvents to total 100%. Preferably, the ratio of the antigelation agent to imidazolinyl benzoic acid, or ester or salt thereof, is about 0.05:1 to 0.5:1.

Preferred herbicidal emulsifiable suspension concentrate compositions of the present invention are those comprising about 10% to 15% by weight imidazolinyl benzoic acid, or ester or salt thereof, about 15% to 25% by weight of a dinitroaniline herbicide, about 2% to 6% by weight of an alkylarylsulfonate, about 1% to 5% by weight of an antigelation agent, about 5% to 10% by weight of a polyoxyethylene phenyl ether, about 0.5% to 2% by weight of a polyalkylene glycol ether, about 1% to 6% by weight of a clay, up to about 1% by weight of an antifoaming agent, up to about 2% by weight xylene, and an aromatic hydrocarbon solvent having a distillation range of from about 135° C. to 305° C. The ratio of the antigelation agent to imidazolinyl benzoic acid, or ester or salt thereof, is more preferably about at 0.1:1 to 0.3:1.

Advantageously, it has been found that the compositions of the present invention which incorporate an antigelation agent, such as N-methylpyrrolidone, provide physically and chemically stable herbicidal emulsifiable suspension concentrate compositions of imidazolinyl benzoic acids, or esters or salts thereof, and dinitroaniline herbicides which remain free-flowing and homogeneous at low temperatures. Such compositions also remain physically and chemically stable after repeated freezing and thawing cycles without precipitating insoluble solids.

Imidazolinyl benzoic acids, or esters and salts thereof, suitable for use in the compositions of the invention include those described in U. S. Pat. No. 4,188,487, the disclosure of which is incorporated herein by reference. Imazamethabenz-methyl is preferred. Dinitroaniline herbicides suitable for use in the compositions of the present invention include those described in U.S. Pat. No. 3,920,742, the disclosure of which is incorporated herein by reference. Preferred are pendimethalin, trifluralin, benfluralin, isopropalin, ethalfluralin, oryzalin and the like with pendimethalin and trifluralin being most preferred.

Alkylarylsulfonates suitable for use in the compositions of the present invention include $C_8$–$C_{18}$alkylbenzenesulfonates, with calcium dodecylbenzenesulfonate being most preferred.

Antigelation agents that are suitable for use in the compositions of the present invention include polar solvents such as N-methylpyrrolidone and cyclohexanone, alcohols such as ethanol and methanol, glycols, such as propylene glycol and ethylene glycol, and the like, with N-methylpyrrolidone preferred. Most preferably, the antigelation agent is present in an amount such that its ratio to the imidazolinyl benzoic acid, or ester or salt thereof, is about 0.05:1 to 0.5:1 to ensure that the compositions remain free-flowing at low temperatures.

Nonionic surfactants suitable for use in the compositions of the present invention include polyalkylene glycol ethers such as butoxypolypropylenoxy polyethylenoxyethanol and the like, and polyoxyethylene phenyl ethers such as polyoxyethylene nonylphenyl ethers, polyoxyethylene dinonylphenyl ethers, polyoxyethylene dodecylphenyl ethers, polyoxyethylene octylphenyl ethers, polyoxyethylene tridecylphenyl ethers and the like, with polyoxyethylene nonylphenyl ethers with about 11 moles of ethylene oxide per molecule being preferred.

Suspending agents suitable for use in the compositions of the present invention include clays such as attapulgite clays, montmorillonite clays, kaolin clays, zeolite, silicas and the like, with attapulgite clays being most preferred.

Organic solvents suitable for use in the compositions of this invention include aromatic hydrocarbon solvents such as toluene, xylenes, polynuclear aromatic hydrocarbons such as naphthalenes and alkylnaphthalenes and mixtures thereof, many of which are available from the fractionation of crude oil and in general have distillation ranges in the temperature range of from about 135° C. to 305° C., with those having a distillation range of from about 183° C. to 290° C. being most preferred, and are commercially available under a variety of tradenames.

The herbicidal emulsifiable suspension concentrate compositions of the present invention may conveniently be prepared by admixing a dinitroaniline herbicide with a mixture of the desired alkylarylsulfonate, nonionic surfactant or mixture of nonionic surfactants, anti-foaming agent and aromatic solvent or mixture of aromatic solvents and the antigelation agent(s) until a homogeneous mixture is obtained, then imazamethabenz-methyl, or other imidazolinyl benzoic acids, or esters or salts thereof, and the desired suspending agent are added to the homogeneous mixture and mixing is continued followed optionally by milling to obtain the desired herbicidal suspension concentrate composition of the present invention.

The following examples are provided to further illustrate the compositions of the present invention but are not intended to limit the invention described herein.

EXAMPLES 1-10

Preparation of emulsifiable suspension concentrate compositions

An aromatic hydrocarbon mixture ($C_{10}$–$C_{13}$) aromatics having a distillation range of from about 229° C.-284° C. (SOLVESSO® 200, Exxon) (17,335 g, 49.5% on a weight basis), N-methylpyrrolidone (660 g, 1.9% on a weight basis), a nonylphenolethoxylate with an average 11 moles of ethylene oxide (ARKOPAL® N110, Hoechst) (2,630 g, 7.5% on a weight basis), calcium dodecylbenzene sulfonate (SOPROPHOR® 70, Rhone-Poulenc) (1.580 g, 60% in isobutanol, 4.5% on a weight basis), a silicone antifoam (SILOCOLAPSE® 431, ICI) (100 g, 0.3% on a weight basis), and a butoxypolypropylenoxy polyethylenoxyethanol (TERGITOL® XD, Union Carbide) (330 g, 0.9% on a weight basis) a, 0.3% on a re stirred together to obtain a homogenous mixture. Molten pendimethalin (technical material, 91.8%, 71.60 g, 20.5% on a weight basis) is added to the homogenous mixture and stirring is continued. Imazamethabenz-methyl (technical material, 93.8% 4,380, 12.5% on a weight basis) and attapulgite clay (ATTAGEL® 50, Engelhard) (825 g, 2.4% on a weight basis) are added to the pendimethalin mixture and stirring is continued. The resultant mixture is stirred with a high-shear mixer and milled to obtain the desired emulsifiable suspension concentrate composition identified as example 1 in Table I.

Using essentially the same procedure, the emulsifiable suspension concentrate compositions identified as compositions 1-10 in Table I are obtained.

TABLE 1

| Ingredient (% wt/wt | EXAMPLES 1-10 | | | | | | | | | |
|---|---|---|---|---|---|---|---|---|---|---|
| | 1 | 2 | 3 | 4 | 5 | 6 | 7 | 8 | 9 | 10 |
| Imzamethabenz-methyl (93.8%) | 12.5 | 12.5 | 12.9 | 12.3 | 12.3 | 12.9 | 12.1 | 12.1 | 12.1 | 11.7 |
| Pendimethalin (91.8%) | 20.5 | 21.2 | 20.8 | 20.8 | 20.8 | 20.8 | 20.8 | 20.8 | 20.8 | 19.5 |
| N-methyl-pyrrolidone | 1.9 | 1.9 | 1.4 | 1.4 | 1.9 | 1.9 | 1.0 | 1.9 | 2.3 | 1.9 |
| ARKOPAL ® N110 | 7.5 | 7.5 | 7.6 | 7.6 | 7.6 | 7.6 | 7.6 | 7.6 | 7.6 | 7.5 |
| TERGITOL ® XD | 0.9 | 0.9 | 0.9 | 0.9 | 0.9 | 0.9 | 0.9 | 0.9 | 0.9 | 0.9 |
| SOPROPHOR ® 70 | 4.5 | 4.5 | 4.5 | 4.5 | 4.5 | 4.5 | 4.5 | 4.5 | 4.5 | 4.5 |
| ATTAGEL ® 50 | 2.4 | 2.4 | 2.4 | 2.4 | 2.4 | 2.4 | 2.4 | 2.4 | 2.4 | 2.4 |
| SILCOLPSE ® 431 | 0.3 | 0.3 | 0.3 | 0.3 | 0.3 | 0.3 | 0.3 | 0.3 | 0.3 | 0.3 |
| Xylene | — | 1.0 | 1.0 | 1.0 | 1.0 | 1.0 | 1.0 | 1.0 | 1.0 | 1.0 |
| SOLVESSO ® 200 | 49.5 | 47.8 | 48.2 | 48.8 | 48.3 | 43.7 | 49.4 | 48.5 | 48.1 | 50.3 |

What is claimed is:

1. A herbicidal emulsifiable suspension concentrate composition comprising about 5% to 20% by weight of a imidazolinyl benzoic acid, or ester or salt thereof, about 10% to 30% by weight of a dinitroaniline herbicide, about 2% to 10% by weight of an akylaryhsulfonate, about 0.5% to 10% by weight of an antigelation agent, about 5% to 15% by weight of a nonionic surfactant or mixture of nonionic surfactants, about 1% to 10% by weight of a suspending agent, up to about 1% by weight of an antifoaming agent, and an aromatic solvent or mixture of aromatic solvents.

2. The composition according to claim 1 wherein the imidazolinyl benzoic acid, or ester or sale thereof, comprises imazamethabenz-methyl.

3. The composition of claim 1 wherein the ratio of the antigelation agent to imazamethabenz-methyl is about 0.05:1 to 0.5:1.

4. The composition according to claim 3 which comprises about 10% to 15% by weight imaza-methabenz-methyl, about 15% to 25% by weight of a dinitroaniline herbicide, about 2% to 6% by weight of an alkylarylsulfonate, about 1% to 5% by weight of an antigelation agent, about 5% to 10% by weight of a polyoxyethylene phenyl ether, about 0.5% to 2% by weight of a polyalkylene glycol ether, about 1% to 6% by weight of a clay, up to about 1% by weight of an antifoaming agent, up to about 2% by weight xylene, and an aromatic hydrocarbon solvent having a distillation range of from about 135° C. to 305° C., wherein the ratio of the antigelation agent to imazamethabenz-methyl is about 0.1:1 to 0.3:1.

5. The composition according to claim 1 wherein the dinitroaniline herbicide is selected from the group consisting of pendimethalin, trifluralin, benfluralin, isopropalin, ethalfluralin and oryzalin.

6. The composition according to claim 5 wherein the dinitroaniline herbicide is pendimethalin.

7. The composition according to claim 1 wherein the alkylarylsulfonate is a $C_8$-$C_{18}$ alkylbenzenesulfonate, the antigelation agent is N-methylpyrrolidone, the nonionic surfactant is a mixture of a polyoxyethylene phenyl ether and a polyalkylene glycol ether, and the suspending agent is a clay.

8. The composition according to claim 7 wherein the $C_8$-$C_{18}$-alkylbenzenesulfonate is calcium dodecylbenzenesulfonate, the antigelation agent is N-methylpyrrolidone, the polyoxyethylene phenyl ether is a polyoxyethylene nonylphenyl ether with about 11 moles of ethylene oxide per molecule, the polyalkylene glycol ether is a butoxypolypropylenoxy polyethylenoxyethanol and the clay is an attapulgite clay.

9. The composition according to claim 1 wherein the aromatic solvent is a mixture of xylene and an aromatic hydrocarbon solvent having a distillation range of from about 135° C. to 305° C.

10. The composition according to claim 9 wherein the aromatic hydrocarbon solvent has a distillation range of from about 183° C. to 290° C.

11. The composition according to claim 1 wherein the antigelation agent is N-methylpyrrolidone.

12. The composition according to claim 1 wherein the aromatic solvent is an aromatic hydrocarbon solvent having a distillation range of from about 135° C. to 305° C.

13. The composition according to claim 11 wherein the aromatic hydrocarbon solvent has a distillation range of from about 183° C. to 290° C.

* * * * *